United States Patent [19]
Loccufier et al.

[11] Patent Number: 5,998,087
[45] Date of Patent: Dec. 7, 1999

[54] PHOTOGRAPHIC MATERIAL CONTAINING A NEW HYDRAZIDE TYPE

[75] Inventors: Johan Loccufier, Zwijnaarde; Stefaan Lingier, Ossenede; Sabine Emmers, Lommel; Jean-Marie Dewanckele, Drongen; Pierre De Clercq, Gent; Noël Hosten, Brugge; Dirk Van Haver, Sint-Niklaan, all of Belgium

[73] Assignee: Agfa-Gevaert, N.V., Mortsel, Belgium

[21] Appl. No.: 09/235,396

[22] Filed: Jan. 22, 1999

[30] Foreign Application Priority Data

Jul. 2, 1996 [BE] Belgium ................................ 96201837

[51] Int. Cl.[6] .................................................. G03C 5/315
[52] U.S. Cl. ........................ 430/264; 430/566; 430/598; 544/300; 546/134; 546/144; 546/316
[58] Field of Search ..................... 430/264, 598, 430/566; 546/134, 144, 316; 544/300

Primary Examiner—Janet Baxter
Assistant Examiner—Amanda C. Walke
Attorney, Agent, or Firm—Breiner & Breiner

[57] ABSTRACT

A silver halide photographic material is disclosed containing a new type of hydrazide compounds represented by following general formula I, the different symbols of which are defined in the description.

formula I

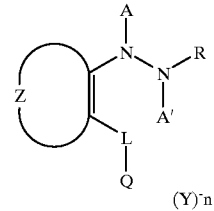

In a preferred embodiment Q is chosen from pyridinium, quinolinium or isoquinolinium. In a most preferred embodiment Q is a pyridinium substituted on the $N^+$ with a $C_5$ to $C_8$ alkyl group.

The photographic material is preferably a graphic arts recording material. High gradation and excellent hard dot quality are obtained.

9 Claims, No Drawings

PHOTOGRAPHIC MATERIAL CONTAINING A NEW HYDRAZIDE TYPE

DESCRIPTION

1. Field of the Invention

The present invention relates to photographic materials, especially graphic arts materials, giving rise to improved gradation and image quality.

2. Background of the Invention

In graphic arts reproduction processes the original image appearing to have a continuous tone gradation is reproduced by a collection of a large number of dots and/or lines. The tone of the reproduced image is influenced by both the size of the dots and lines and their density. A graphic arts film exposed in a way to exactly render the relative proportions of black and white in the original must produce dots and lines of sufficient density; another reason herefore is the fact that no substantial amount of copying light may be transmitted through the dots and lines in a further duplicating cycle. Therefore a photographic element showing high contrast or so-called "lith gradation" on development is highly desired. Furthermore the generated or reproduced dots and lines must exhibit a well-shaped form and sharp edges.

This most desired combination of high contrast and excellent dot quality is commonly termed "lith quality". The goal of achieving optimal lith quality is reached by the combination of specially designed graphic arts material and appropriate processing systems. A first group of such processing systems consists of the traditional "lith developers" characterized by the presence of hydroquinone as the sole developing agent and a low but critical sulphite ions content giving rise to an infectious development mechanism, as was described by Yule in *The Journal of the Franklin Institute*, Vol. 239, p. 221–223, (1945). This type of development is believed to proceed autocatalytically. The low concentration of sulphite is maintained by the progressive dissociation of an aldehyde-bisulphite adduct. However these conventional lith developers are rather instable in time and require complicated replenishment systems for both oxidation and exhaustion. Furthermore their developing capacity is limited due to the fact that they contain hydroquinone as the sole developing agent.

In more recent times so-called "hard dot Rapid Access" developers were introduced on the market which combine a good stability with a "lith quality" in the reproduction of lines and screen dots. Examples of such developers and corresponding appropriate photographic materials include the GRANDEX system, marketed by FUJI PHOTO ltd., AGFASTAR, marketed by AGFA-GEVAERT N. V. and the ULTRATEC system, marketed by EASTMAN KODAK Co. Some of these systems make use of the contrast promoting action, induced by a nucleating mechanism, of hydrazine derivatives known for long time in the photographic art. As described by Simson et al., U.S. Pat. No. 4,650,746, use of a hydrazine compound permits the use of an auxiliary development agent in combination with the hydroquinone type of developing agent so that the development capacity can be increased. It also permits the presence of a relatively high sulphite concentration in order to protect the developer against aerial oxidation and thereby prolonging its effective working life.

Further early disclosures on hydrazine compounds, incorporated either in a photographic element or in a developing solution, include Smith U.S. Pat. No. 2,410,690, Stauffer U.S. Pat. No. 2,419,974, Trivelli U.S. Pat. No. 2,419,975 and Hunsberger U.S. Pat. No. 2,892,715 and an article by Stauffer, Smith and Trivelli entitled "The influence of photographic developers containing hydrazine upon the characteristic curves of photographic materials", *The Journal of the Franklin Institute*, Vol. 238, p. 291–298, October 1944. Since then the photographic world has undertaken extensive research on hydrazine chemistry for use in photographic applications and the recent patent literature on new hydrazine derivatives and on the combination of known or new hydrazines with other useful ingredients in photographic elements or developers is abundant.

A practical early recognized problem was caused by the high pH levels needed for the developers containing hydrazine compounds or used with photographic elements containing these compounds in order to get the maximum effect on contrast. The teaching of Nothnagle U.S. Pat. No. 4,269,929 brought a solution to this problem. Here a method for high contrast development was disclosed involving a hydrazine compound, either in the photographic element or in the developer, said developer further containing a hydroquinone developing agent, a 3-pyrazolidinone developing agent, sulphite ions, and a "contrast-promoting amount" of an amino compound. In a preferred embodiment the hydrazine compound was incorporated in the photographic material. According to this patent, issued May 26, 1981, this particular combination of ingredients allow the use of a rather moderate alkaline pH for the developing solution while retaining the desired high contrast and dot quality characteristics. In this way an excellent combination of lith quality of the finished material, high developing capacity and long effective life of the developer was achieved.

Since then intense research has been conducted to improve the performance of hydrazines, mostly acylhydrazides, and in particular to make them workable in combination with conventional rapid access developers having a pH around 10.5 and containing no special ingredients such as amine boosters. Specific new hydrazide derivatives are described, e.g. in JP-A 57-99635, EP 0 217 310, JP-A 61-270744, JP-A 62-89958, EP 0 283 040, EP 0 301 799, U.S. Pat. No. 4,816,373, U.S. Pat. No. 4,847,180, JP-A 63-294552, JP-A 63-44649, JP-A 63-8715, EP 0 283 040, JP-A 01-100530, EP 0 345 025, JP-A 01-201650, EP 0 356 898, DE 38 29 078, U.S. Pat. No. 4,950,578, U.S. Pat. No. 5,028,510, EP 0 399 460, U.S. Pat. No. 5,006,445, JP-A 01-285940, U.S. Pat. No. 4,988,604, U.S. Pat. No. 4,994,365, JP-A 02-300474, JP-A 02-302750, JP-A 02-841, JP-A 02-947, EP 0 444 506, EP 0 479 156, JP-A 04-283743, EP 0 539 925 and U.S. Pat. No. 5,212,045.

A study on the nucleating mechanism of acylhydrazides, responsible for infectious development, can be find in Simson, SPSE, 25th Fall Symposium, (1985), p. 48. Other studies include Kitchin et al., J. Phot. SCi., Vol. 35, (1987), p. 162, Shinoara et al., J. Photogr. Sci., Vol. 35, (1987), p. 181, and Kobayashi, J. Phot. Sci., Vol. 43, (1995), p. 186.

An important technological breakthrough was the development and use of sulphonamido-arylhydrazides as disclosed in EP 0 286 840 and U.S. Pat. No. 5,104,769, which proved to be a very reactive and effective type. Another main progress was the use of hydrazides, especially sulphonamido-arylhydrazides in combination with so-called "incorporated boosters", such as disclosed in Machonkin U.S. Pat. No. 4,975,354, which can be incorporated into the photographic material itself instead of the developer. Still other graphic arts systems are based on the use of hydrazine types that can release a photographically useful group, e.g. an accelerator or a development restrainer, such as disclosed in e.g. EP 0 393 720, EP 0 393 721, EP 0 399 460, U.S. Pat. No. 5,258,259, EP 0 420 005, U.S. Pat. No. 5,252,438 and U.S. Pat. No. 5,262,274.

The present invention extends the teachings on hydrazine compounds in photographic silver halide materials.

It is an object of the present invention to provide a new class of reactive hydrazines for use in a photographic material.

It is a further object of the present invention to provide a photographic material, in particular a graphic arts recording material, showing high gradation and excellent quality of reproduced dot and line patterns, without the need for a special booster in the film or the developing solution.

3. Summary of the Invention

The objects of the present invention are realized by providing a photographic material comprising a support, at least one emulsion layer, and optionally one or more other hydrophilic layers, characterized in that said emulsion layer or another hydrophilic layer adjacent to said emulsion layer contains a compound according to general formula I:

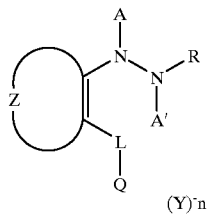

(Formula I)

wherein

1) R represents a member selected from the group consisting of $COR^1$, $SO_2R^2$, $SOR^3$, $POR^4R^5$ and $COCOR^6$; each of $R^1$ and $R^6$ independently represents hydrogen, an alkyl group, an aryl- or heteroarylgroup, $OR^7$, or $NR^8R^9$; each of $R^2$ and $R^3$ independently represents an alkylgroup, an aryl- or heteroarylgroup, $OR^7$ or $NR^8R^9$; each of $R^4$ and $R^5$ indepedently represents one of the significances given for $R^2$ or they may constitute together the necessary atoms to close a ring; R7 represents an alkylgroup, an aryl- or heteroarylgroup; each of $R^8$ and $R^9$ independently represents hydrogen, an alkyl group or an aryl- or heteroarylgroup or they may constitute together the necessary atoms to form a ring;

2) each of A and A' independently represent hydrogen, a group capable of yielding hydrogen under alkaline photographic processing conditions or a $SO_2R^{10}$ group, provided that, if A is $SO_2R^{10}$, A' is a hydrogen and vice versa; $R^{10}$ has one of the significances given for $R^2$;

3) L is a divalent linking group consisting of a linear chain having at most two atoms in said chain;

4) Q is a cationic nitrogen containing aromatic heterocyclic ring;

5) $Y^-$ is a negatively charged counterion to compensate the positive charge of Q;

n is 0 if the compound according to formula I is an inner salt or an integer equal to the positive charge of Q, and 6) Z represents the necessary atoms to form an aromatic or heteroaromatic ring.

In a most preferred embodiment Q is chosen from pyridinium, guinolinium and isoquinolinium. In a most preferred embodiment Q is pyridinium substituted on the quaternary nitrogen with a $C_5$ to $C_8$ alkyl group.

Preferably, the photographic material is a graphic arts material, most preferably a graphic arts recording material.

4. Detailed Description

Typical examples of compounds according to general formula I are given below.

N-I

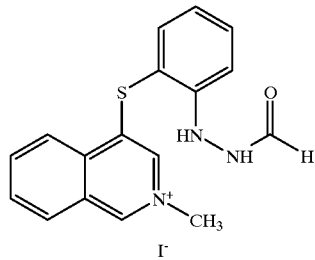

N-II

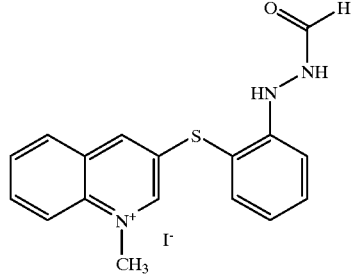

-continued
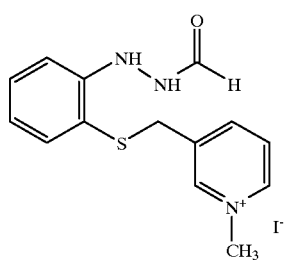
N-III
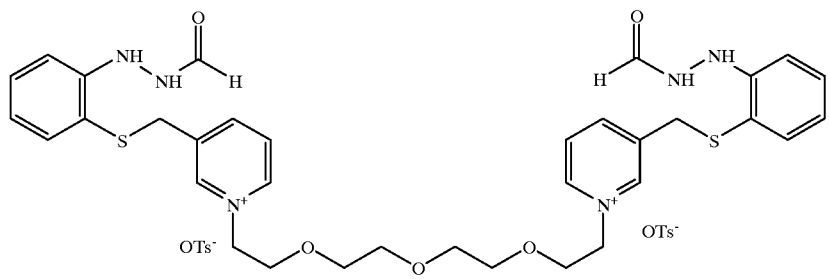
N-IV
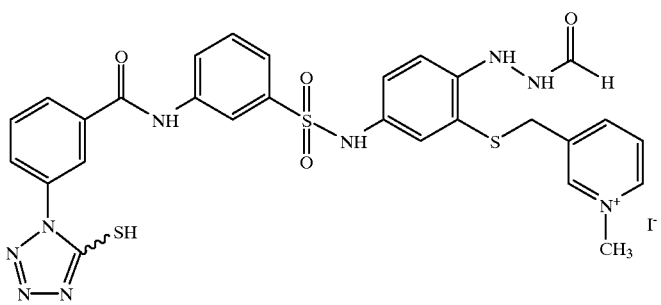
N-V
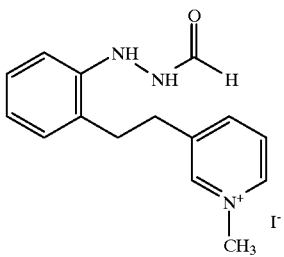
N-VI
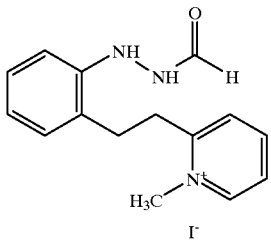
N-VII -continued
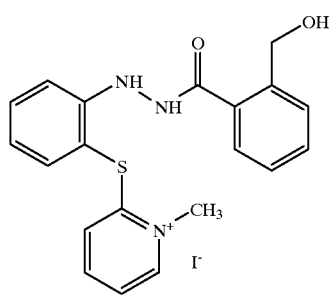
N-VIII
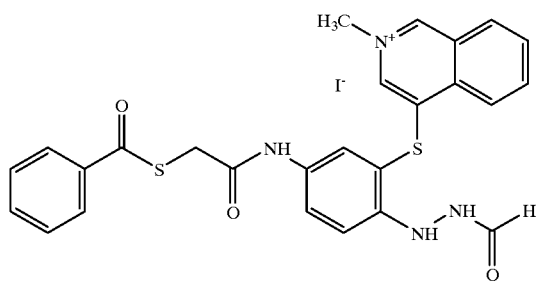
N-IX
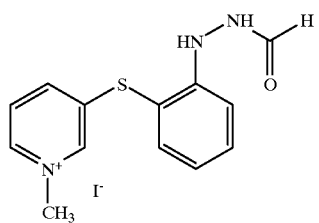
N-X
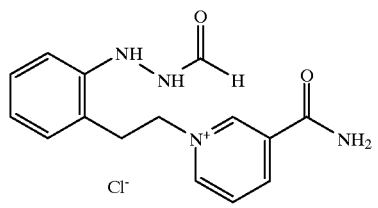
N-XI
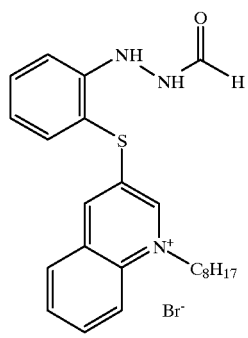
N-XII -continued
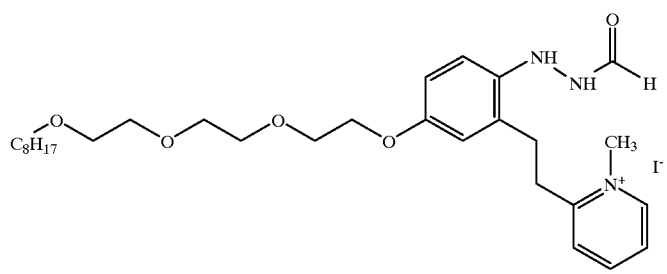
N-XIII
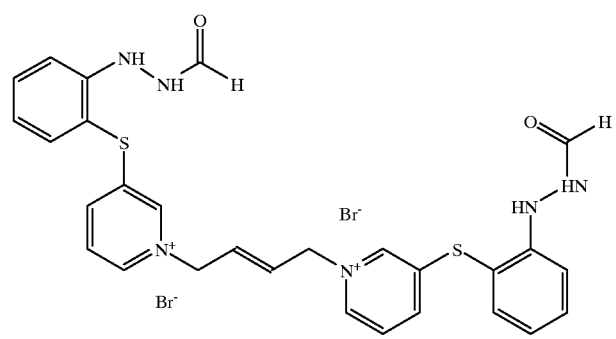
N-XIV
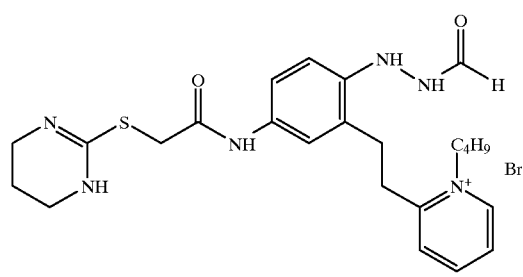
N-XV
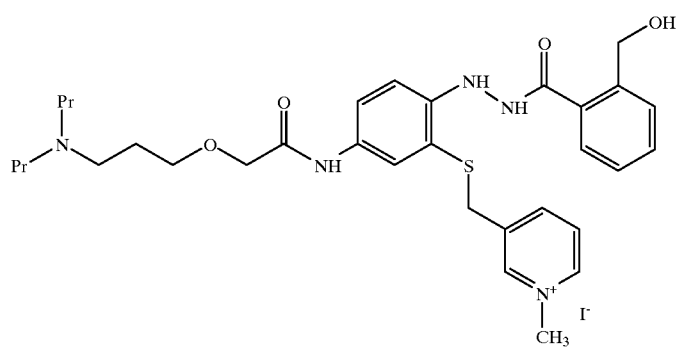
N-XVI
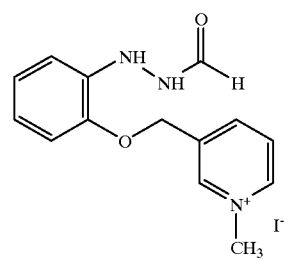
N-XVII

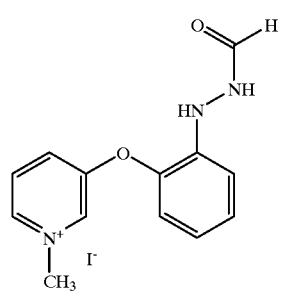
N-XVIII
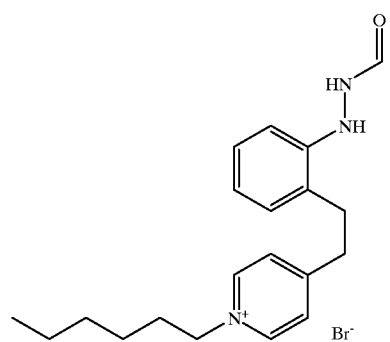
N-XIX
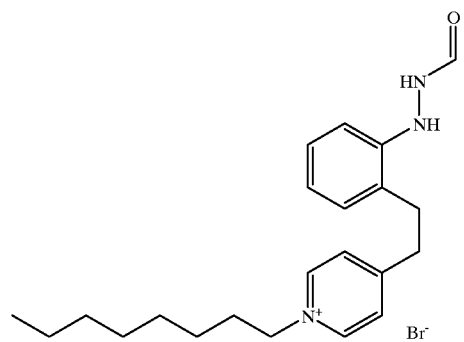
N-XX
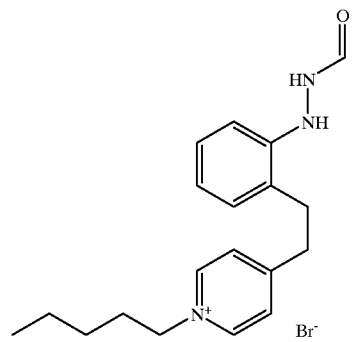
N-XXI

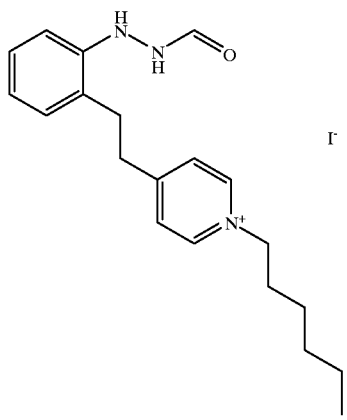

N-XXII

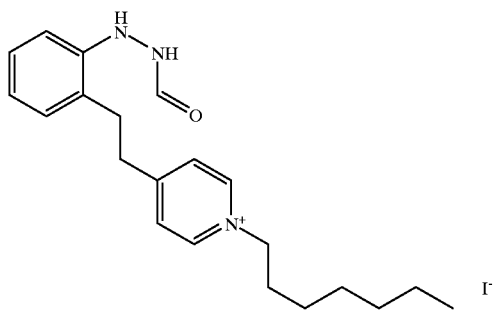

N-XXIII

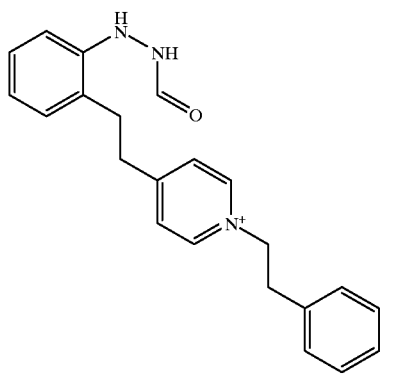

N-XXIV

From this list the compounds N-XIX to N-XXIV are the most preferred. It will be clear that a mixture of two or more nucleating agents can be used. For instance, one of the preferred compounds chosen from N-XIX to N-XXIV can be mixed with another hydrazide.

We will now explain in detail the synthesis of some of the hydrazine nucleators of the present invention.

The synthesis of nucleating agent N-I

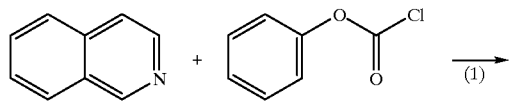
(1)

-continued
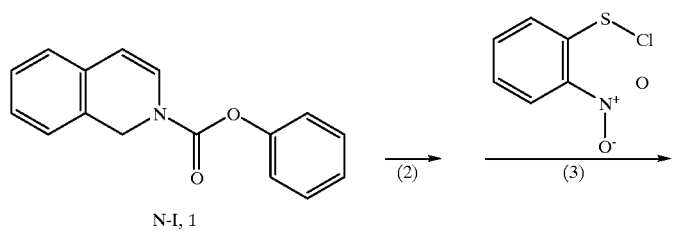
N-I, 1
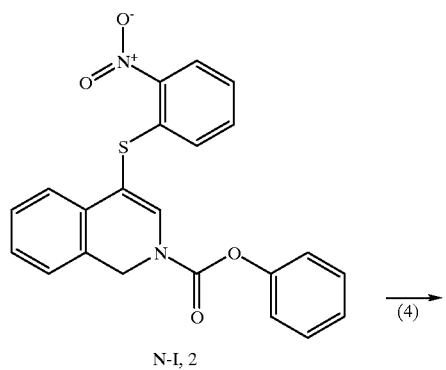
N-I, 2
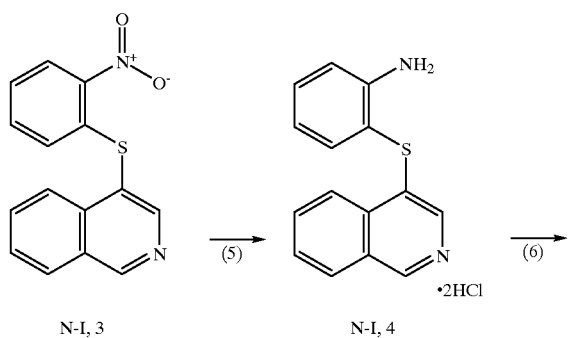
N-I, 3    N-I, 4
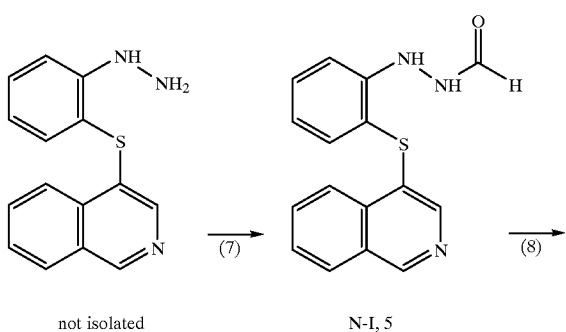
not isolated    N-I, 5

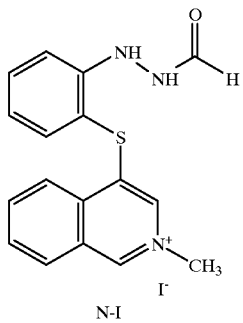

(1) NaBH$_4$, THF, 0° C.;
(2) CH$_2$Cl$_2$, RT;
(3) DDQ, THF;
(4) RaNi, H$_2$, HCl (conc.);
(5) NaNO$_2$, HCl, SnCl$_2$, HCl, NaOH, extraction;
(6) MeOOCH, reflux;
(7) MeI, acetone, reflux The synthesis of intermediate N-I,1

195 g (1.5 mol) of isoquinoline was dissolved in 2 l of t.butyl-methyl-ether. 66.6 g (1.8 mol) of NaBH$_4$ was added and the reaction mixture was cooled to −5° C. 192 ml (1.535 mol) of phenyl chloroformate was added while the temperature was kept below 0° C. The reaction was allowed to continue for 1 hour at 0° C. The mixture became very difficult to stir. The reaction mixture was carefully pourred into 7.5 l of water. The mixture was extracted with 4 l of methylene chloride. The organic phase was dried over sodium sulphate and evaporated under reduced pressure. The oily residue was crystallized from 600 ml of ethanol. Cooling to 5° C. was favourable for the yield (m.p.: 98° C.)

The synthesis of intermediate N-I,2

125 g (0.5 mol) of N-I,1 was dissolved in 500 ml of methylene chloride. 99.5 ml of 2-nitrophenyl-sulfenyl chloride was added over 20 minutes. After an endothermic reaction, the reaction mixture was stirred for 3 hours at room temperature. The reaction mixture was concentrated to one fifth of its volume and 300 ml of methanol was added. The product precipitated and was isolated by filtration (m.p. 145° C.).

The synthesis of intermediate N-I,3

84.5 g (0.209 mol) of N-I,2 was dissolved in 420 ml of THF. 54.56 g (0.24 mol) of 2,3-dichloro-5,6-dicyano-1,4-quinone was added while gently cooling. The reaction was allowed to continue for 1 hour at room temperature. The reaction mixture was pourred into a 400 ml of a 1N NaOH-solution and extracted with 400 ml of methylene chloride. The methylene chloride fraction was washed with a 0.1N NaOH-solution and dried over MgSO$_4$. The methylene chloride was evaporated under reduced pressure and the crude product was purified with preparative column chromatography (eluent: CH$_2$Cl$_2$-ethyl acetate 95-5, m.p.= 172° C.).

The synthesis of intermediate N-I,4

32.4 g (0.115 mol) of N-I,3 was dissolved in 360 ml of 1-methoxy-2-propanol. Raney-Ni was added as catalyst and N-I,3 was hydrogenated at 80° C. The catalyst was removed by filtration and 24 ml of concentrated HCl was added. The product precipitated from the medium and was isolated by filtration (sublimation at 190° C.).

The synthesis of the intermediate N-I,5

21,14 g (65 mmol) of intermediate N-I,4 was suspended in 50 ml of concentrated hydrochoric acid. The mixture was cooled to −5° C. and a solution of 4.49 g (65 mmol) of NaNO$_2$ in 10 ml water was added over 25 minutes, while the temperature was kept at 0° C. The reaction mixture was additionally stirred for 30 minutes at 0° C. After 30 minutes, a suspension of 59.02 g (0.26 mol) of SnCl$_2$.2H$_2$O in 75 ml of concentrated hydrochloric acid was added over one hour, while the temperature was kept at 0° C. The reaction mixture was stirred for 1 hour at 0° C. After 1 hour the solution was neutralized with a 10 N NaOH-solution. The precipitate was isolated by filtration and treated with 250 ml of methylene chloride. The methylene chloride solution of the hydrazine was filtered to remove inorganic residues, treated with MgSO$_4$, filtered again and evaporated under reduced pressure. 18 g of the crude hydrazine was dissolved in 65 ml of methyl formate and the reaction mixture was refluxed for 12 hours. The intermediate N-I,5 precipitated from the medium and was isolated by filtration. (mp: 160° C.).

The synthesis of nucleating agent N-I 7.39 g (28 mmol) of N-I,5 was dissolved in 125 ml of acetone. The reaction mixture was kept under an inert atmosphere. 3.15 ml (50 mmol) of methyl iodide was added and the reaction mixture was refluxed for 2 hours. After 2 hours 3.15 ml (50 mmol) of methyl iodide was added and the reaction mixture was refluxed again for 2 hours. A yellow coloured precipitate was formed. The precipitated product was isolated by filtration and recrystallized from methanol (m.p.: 210° C. (dec.)). (During alkylation, sometimes a dark oil precipitated first before the product precipitated as a solid from the reaction mixture. The oily residue could be crystallized from methanol.)

The synthesis of nucleating agent N-III

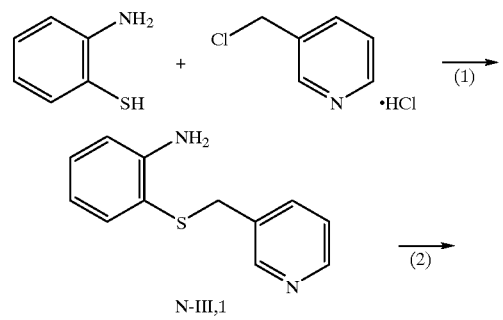

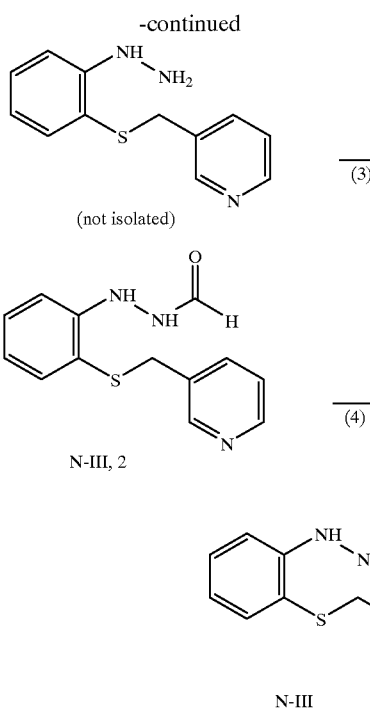

(1) KOH, EtOH;
(2) NaNO₂, HCl, SnCl₂, HCl, NaOH, extraction;
(3) MeOOCH, reflux;
(4) MeI, acetone, reflux The synthesis of intermediate N-III,1

29.1 g of KOH (85%) was dissolved in 240 ml of ethanol. 50 g (0.4 mol) of 2-aminothiophenol was added. In a separate reaction vessel, 78.8 g (0.48 mol) of 3-picolylchloride chlorohydrate was suspended in 240 ml of ethanol. 29.1 g of KOH was added while the temperature was kept below 35° C. After 15 miutes the 3-picolyl chloride solution was added to the solution of 2-aminothiophenol, while the temperature was kept below 20° C. After one and a half hour, the reaction mixture was poured into 2.5 l of water. The reaction mixture was extracted four times with 500 ml of t.butyl-methyl-ether. The pooled organic fractions were washed with a 25% sodium chloride solution, dried over MgSO₄ and evaporated under reduced pressure. The crude product was purified by preparative column chromathography (eluent: CH₂Cl₂—MeOH: 97-3, Rf: 0.18).

The synthesis of intermediate N-III,2

31 g (0.143 mol) of N-III,1 was dissolved in 140 ml of concentrated HCl. The reaction mixture was cooled to −5° C. A solution of 9.87 g (0.143 mol) of NaNO₂ in 15 ml water was added over 30 minutes while the temperature was kept below 0° C. The reaction was allowed to continue for 30 minutes at 0° C. After 30 minutes a suspension of 97.38 g of SnCl₂.2H₂O (0.429 mol) in 140 ml of concentrated HCl was added while the temperature was kept below 0° C. After 2 hours reaction time at 0° C., an extra 0.22 mol of SnCl₂.2H₂O was added. The reaction was allowed to continue for an extra hour at 0° C. 400 g of ice was added to the reaction mixture. The mixture was made alkaline with 10N NaOH and extracted twice with 400 ml of methylene chloride. The pooled organic fractions were dried over MgSO₄ and evaporated under reduced pressure. The crude hydrazine was used without purification. The crude hydrazine was dissolved in 60 ml of methyl formate and the mixture was refluxed for 16 hours. The reaction mixture was evaporated under reduced pressure and the hydrazide was isolated by preparative column chromatography (eluent: CH₂Cl₂-methanol-hexane: 50-10-40; Rf: 0.5).

The synthesis of nucleating agent N-III 28.3 g (0.109 mol) of N-III,2 was dissolved in 50 ml of acetone. 14.2 ml (0.218 mol) of methyl iodide was added and the reaction was allowed to continue for 24 hours at room temperature. The nucleating agent precipitated from the medium and was isolated by filtration. (Sometimes crystallization of the nucleating agent N-III was difficult. Sometimes the product precipitated as an oil.)

The synthesis of nucleating agent N-VI

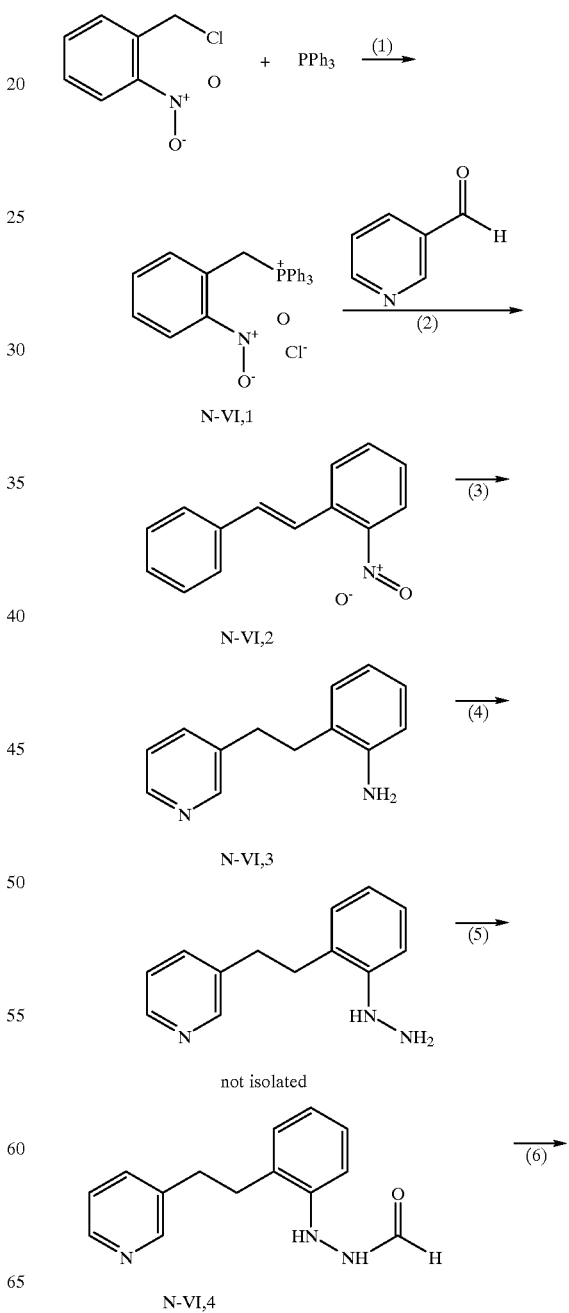

21
-continued

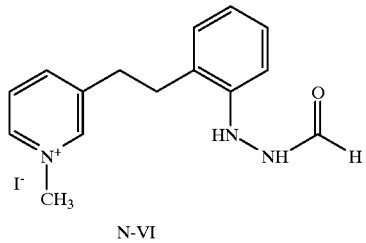

N-VI (1) methoxypropanol, reflux; (2) NaO Me, THF, reflux; (3) Pd/C, EtOH, H₂;
(4) NaNO₂, HCl, CH₂Cl₂, SnCl₂; (5) HCOOET, reflux; (6) MeI, CH₂Cl₂, reflux The synthesis of intermediate N-VI,1

17.1 g (0.1 mol) of 2-nitrobenzyl chloride and 26.2 g (0.1 mol) of triphenylphosphine were melted at 90° C. After 15 minutes the mixture solidified. The solid was crushed into small particles and treated with acetone/ether 1/1. N-VI,1 was isolated by filtration, washed with acetone/ether 1/1 and dried.

The synthesis of intermediate N-VI,2

17.64 g (40.7 mmol) of N-VI,1 was dissolved in 200 ml of THF. 2.40 g (42 mmol) of sodium methylate was added. The solution became dark red. 4.36 g (40.7 mmol) of 3-pyridinecarboxaldehyde was added and the reaction mixture was refluxed for 1 hour. After 1 hour the solution was hardly coloured. The precipitated salts were removed by filtration and the solvent was evaporated under reduced pressure. The product was purified by preparative column chromatography (eluent: ethyl acetate/toluene: 1/1: Rf: 0.47). N-VI,2 was a mixture of the E- and the Z-isomer.

The synthesis of intermediate N-VI,3

6.78 g (30 mmol) of N-VI was dissolved in 250 ml of ethanol. N-VI,3 was hydrogenated over Pd/C at 50° C. The hydrogenation was complete in 1 hour. The catalyst was removed by filtration and the solvent was evaporated under reduced pressure. The aniline was used without further purification.

The synthesis of intermediate N-VI,4

4.4 g (22.2 mmol) of N-VI,3 was dissolved in 150 ml of methylene chloride. 25 ml of concentrated HCl was added. The mixture was cooled to −10° C. 1.67 g (24.2 mmol) of NaNO₂ in 3 ml of water was added while the temperature was kept at −10° C. The reaction mixture was further cooled to −30° C. and 15 g (66.6 mmol) of SnCl₂.2H₂O in 25 ml of concentrated HCl was added. The reaction was allowed to continue for 1 hour at 0° C. and another 2 hours at room temperature. The reaction mixture was neutralized with 5 N NaOH and extracted twice with 200 ml of methylene chloride. The pooled organic fractions were dried over MgSO₄ and evaporated under reduced pressure. The hydrazine was dissolved in ethyl formate and the reaction mixture was refluxed for 20 hours. The solvent was removed under reduced pressure and the hydrazide was isolated by preparative column chromatography using a LICHROPREP RP18 column (Merck) with a gradient elution from methanol/water 30/70 to methanol/water 50/50.

22
The synthesis of nucleating agent N-VII

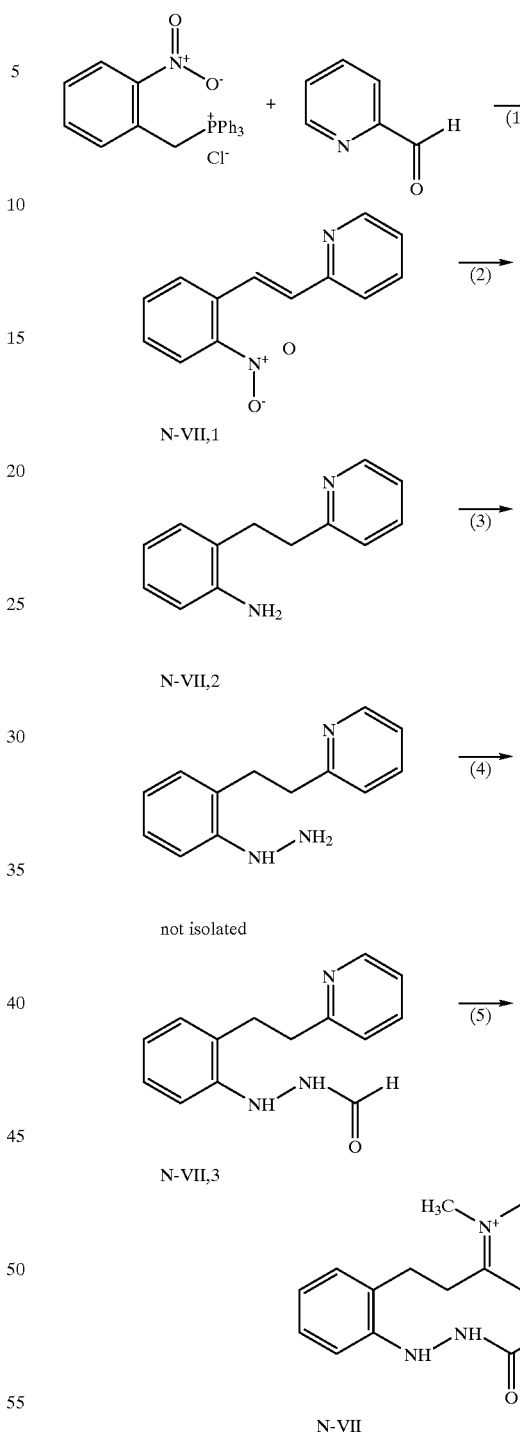

(1) NaO Me, THF, reflux; (2) Pd/C, EtOH, H₂; (3) NaNO₂, HCl, CH₂Cl₂, SnCl₂;(4) HCOOEt, reflux; (5) MeI, CH₂Cl₂, reflux 1.62 g (6.7 mmol) of N-VI,4 was dissolved in 40 ml of methylene chloride and 0.62 ml (10 mmol) of methyl iodide was added. The mixture was heated to 70° C. under pressure and the reaction was allowed to continue for 3 hours. The product precipitated as an oil. The oily residue was crystallized with some difficulty from isopropanol with a small percentage of methanol. The synthesis of nucleating agent N-VII The synthesis of intermediate N-VII,1

N-VII,1 was prepared in the same way as N-VI,2. The product was purified by preparative column chromatography (eluent: ethyl acetate/toluene 1/1: Rf: 0.64)

The synthesis of intermediate N-VII,2

The reduction of N-VII,1 was carried out in the same way as the reduction of N-VI,3. The aniline N-VII,2 was used without further purification.

The synthesis of intermediate N-VII,3

6.3 g (31.8 mmol) of N-VII,2 was dissolved in 150 ml of methylene chloride. 40 ml of concentrated HCl was added and the reaction mixture was cooled to −15° C. A solution of 2.42 g (35 mmol) of NaNO$_2$ in 5 ml of water was added slowly while the temperature was kept below −10° C. After 20 minutes 21.6 g of SnCl$_2$.2H$_2$O in 35 ml of concentrated HCl was added slowly while the temperature was kept below −20° C. The reaction was allowed to continue for 2 hours at room temperature. The reaction mixture was neutralized with 5 N NaOH and extracted twice with 200 ml of methylene chloride. The pooled organic fractions were dried over MgSO$_4$ and evaporated under reduced pressure. The hydrazine was used without further purification. The oily residue was dissolved in 40 ml of ethyl formate and the reaction mixture was heated to 80° C. under pressure. After 3 hours, the solvent was evaporated and the hydrazide N-VII,3 was purified by preparative column chromatography using a gradient elution from ethyl acetate/toluene 20/80 over ethyl acetate to ethyl acetate/methanol 95/5.

The synthesis of nucleating agent N-VII 2.46 g (10.2 mmol) of N-VII-3 was dissolved in 40 ml of methylene chloride and 0.93 ml (15.3 mmol) of methyl iodide was added. The reaction mixture was heated to 70° C. under pressure. The reaction was allowed to continue over night at 70° C. Nucleating agent N-VII precipitated from the medium. The product was isolated by filtration, washed with methylene chloride and dried.

The synthesis of nucleating agent X

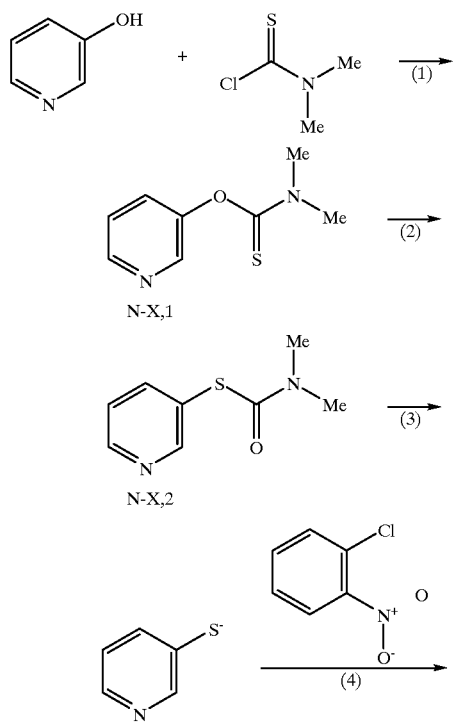

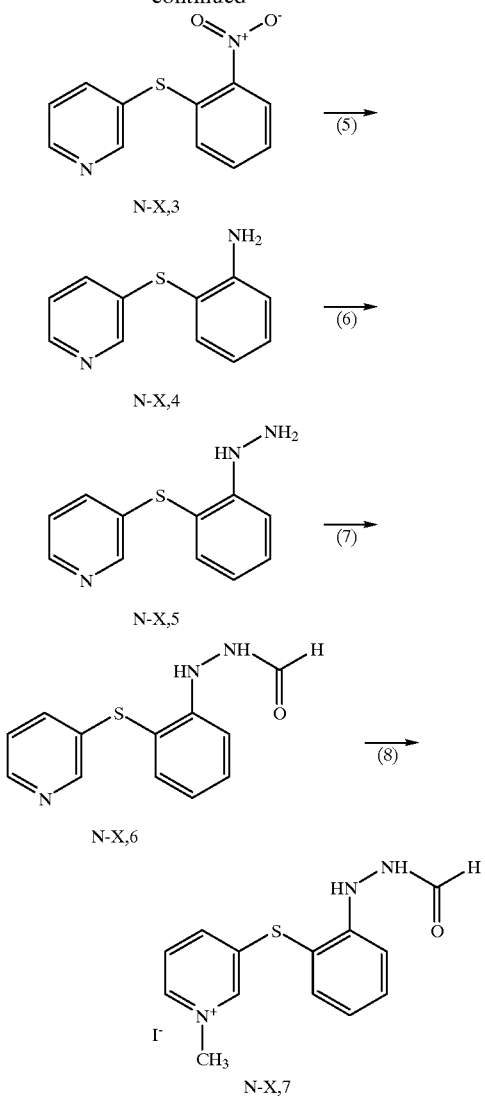

(1) NaH, DMA; (2) 250° C., no solvent; (3), (4) NaOMe, MeOH;
(5) RaNi, EtOAc; (6) NaNO$_2$, HCl, SnCl$_2$, HCl; (7) EtOOCH, reflux;
(8) MeI, acetone, reflux;

The synthesis of intermediate N-X,1

167.5 g (1.763 mol) of 3-hydroxypyridine was dissolved in dissolved in 1300 ml of dimethylacetamide. 70.5 g (1.763 mol) of a 60% NaH dispersion in mineral oil was added in small portions. After the addition was completed, the reaction mixture was stirred for an extra hour. 123.6 g (2.29 mol) of dimethylthiocarbamoyl chloride was added over 5 minutes. The reaction mixture was heated to 80° C. and the reaction was allowed to continue for 1 hour. The reaction mixture was cooled to room temperature and poured into 2.5 l of a 1% KOH-solution. The aqueous layer was extracted four times with 1 liter of toluene. The pooled organic fractions were extracted four times with 750 ml of a 5% HCl-solution. The pooled aqueous fractions were neutralized with a 10% KOH-solution and extracted four times with 750 ml of toluene. The pooled organic fractions were dried over MgSO$_4$ and evaporated under reduced pressure. The product was isolated by vacuum destination of the oily residue. The fraction with a boiling point of 160 to 164° C. at 0.7 mm Hg was isolated.

The synthesis of intermediate N-X,2

247 g (1.35 mol) of N-X,1 was heated to 250° C. for 45 minutes. N-X,2 was isolated by vacuum destination of the residual dark oil. The fraction, boiling at 152° C. at 1 mm Hg, was isolated. The isolated orange oil was further purified by crystallization from t.butyl-methyl ether. A white crystalline product was isolated having a melting point 45° C.

The synthesis of intermediate N-X,3

45.6 g (0.25 mol) of N-X,2 was dissolved in 140 ml of methanol. 50.9 ml of a 30% sodium methylate solution in methanol was added over 15 minutes and the reaction was allowed to continue for 14 hours at room temperature. After 14 hours, a solution of 39.4 g (0.25 mol) of 1-chloro-2-nitrobenzene in 80 ml of methanol was added and the reaction mixture was refluxed for 8 hours. The methanol was evaporated under reduced pressure and the residue was treated twice with 250 ml of water. The orange solid was finally treated twice with 50 ml of t.butyl-methyl-ether. A yellow precipitate was isolated having a melting point of 96° C.

The synthesis of intermediate N-X,4

44 g (0.19 mol) of N-X,3 was dissolved in 700 ml of ethyl acetate. N-X,3 was hydrogenated at room temperature over Raney-Ni as catalyst. After 1 hour, the catalyst was removed by filtration and the ethyl acetate was evaporated under reduced pressure. The oily residu solidified with some difficulty. The solid residue was treated with 60 ml of hexane. A white solid, having a melting point of 60° C., was isolated.

The synthesis of intermediate N-X,6

30.3 g (0.15 mol) of N-X,4 was suspended in 150 ml of ice/water and 35 ml of a concentrated HCl solution was added. The reaction mixture was cooled to –5° C. A solution of 11 g (0.16 mol) of $NaNO_2$ in 50 ml of water was added while the temperature was kept below 0° C. After complete addition the reaction was allowed to continue for 30 minutes at –3° C. A suspension of 101.3 g (0.45 mol) of $SnCl_2.2H_2O$ in 83.3 ml of concentrated HCl-solution was added slowly while the temperature was kept below 0° C. The reaction was allowed to continue for 1 hour at room temperature. After complete reduction the reaction mixture was neutralized with 10 N NaOH. The aqueous reaction mixture was extracted with 250 ml of methylene chloride. The organic layer was filtered over Celite and the aqueous layer was extracted again with 500 ml of methylene chloride. The pooled organic fractions were dried over $MgSO_4$ and evaporated under reduced pressure. The hydrazine N-X,5 was isolated as a solid product having a melting point of 68° C. The hydrazine was used without further purification. The hydrazine N-X,5 was dissolved in 162 ml of ethyl formate. 10 ml of dimethylformamide was added and the mixture was refluxed for 24 hours. After 24 hours the ethyl formate was removed under reduced pressure and the residue was pourred into 100 ml of water. The mixture was extracted twice with 150 ml of methylene chloride. The pooled organic fractions were washed with 150 ml of 25% NaCl-solution and dried over $MgSO_4$. The solvent was evaporated under reduced pressure and the hydrazide was purified by preparative column chromatography (eluent $CH_2Cl_2$-methanol: 95/5, Rf: 0.25).

The synthesis of nucleating agent N-X 7.4 g (30 mmol) of N-X,6 was suspended in 70 ml of acetone. 21.3 g (0.15 mol) of methyl iodide was added and the mixture was refluxed for one and a half hour. The product precipitated as an oil. The acetone was decanted and the residue was treated twice with 100 ml ethyl acetate. On standing overnight the product solidified with some difficulty. The solid residue was finaly treated with 20 ml acetonitrile, yielding the hydrazide N-X, which was easily isolated by filtration (m.p.: 165° C).

The synthesis of nucleating agent N-XVII

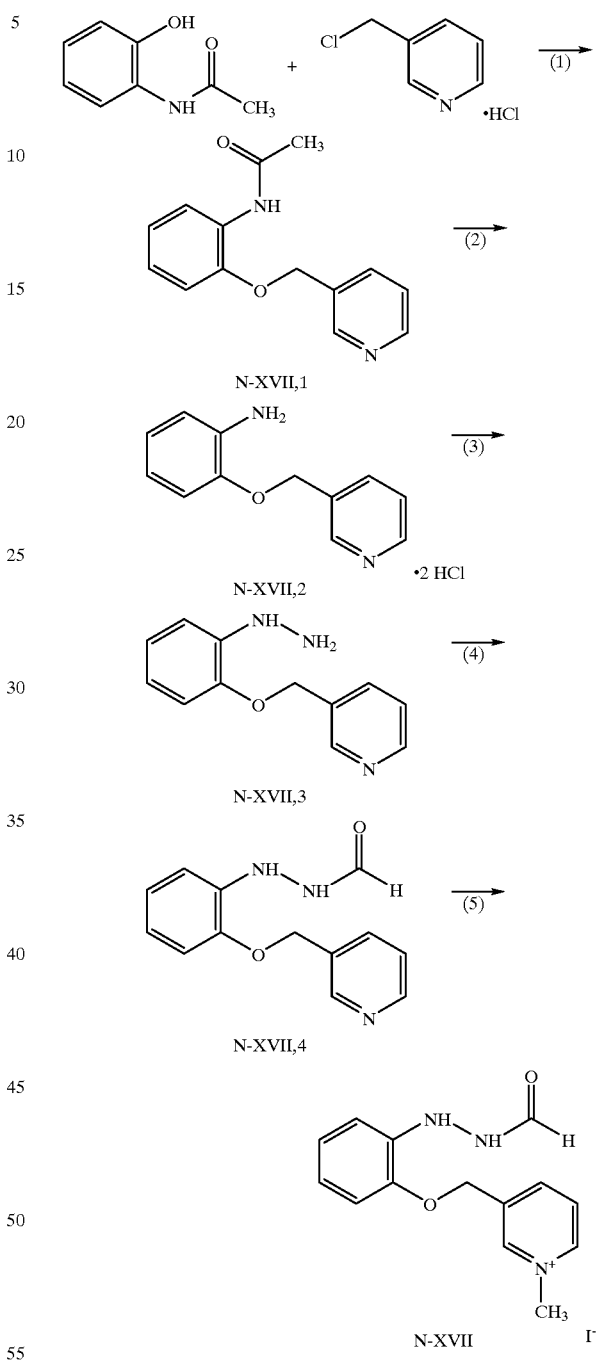

(1) KOH, EtOH; (2) HCl, EtOH, reflux; (3) $NaNO_2$, HCl, $SnCl_2$, HCl, NaOH, extraction; (4) EtOOCH, DMF; (5) MeI, acetone, reflux The synthesis of intermediate N-XVII,1

54.4 g (0.36 mol) of 2-hydroxyacetanilide was suspended in 100 ml of ethanol. A solution of 52.1 g of KOH (85%) in 400 ml of ethanol was added. To this solution, a suspension of 65.6 g (0.40 mol) of 3-picolylchloride chlorohydrate in 150 ml of ethanol was added and the reaction mixture was refluxed for one and a half hour. After one and a half hour the solvent was removed under reduced pressure and the oily residue was treated with 700 ml of water. The precipitated product was isolated by filtration, treated with 200 ml of water/20 ml of ethanol and isolated again by filtration. (m.p.: 113° C).

The synthesis of intermediate N-XVII,2

84.8 g (0.35 mol) of N-XVII,1 was suspended in 250 ml of ethanol. 87.5 ml of concentrated HCl was added and the reaction mixture was refluxed for 5 hours. On cooling the product crystallized from the medium. N-XVII,2 was isolated by filtration, washed with ethanol and dried (m.p. 180° C. with decomposition).

The synthesis of intermediate N-XVII,4

41 g (0.15 mol) of N-XVII,2 was suspended in 60 g of ice and 25 ml of concentrated hydrochloric acid. The suspension was cooled to 0° C. and a solution of 10.4 g (0.15 mol) of $NaNO_2$ in 30 ml of water was added slowly while the temperature was kept below 0° C. After complete addition the reaction was allowed to continue for 45 minutes. A suspension of 101.5 g (0.45 mol) of $SnCl_2.2H_2O$ in 62.5 ml of concentrated hydrochloric acid was added while the temperature was kept below 0° C. After the addition was completed the reaction was allowed to continue for one hour at room temperature. The reaction mixture was neutralized with 10 N NaOH while the temperature was kept below 10° C. When the reaction mixture had a pH of 9, the mixture was extracted with 500 ml of ethyl acetate. Celite was added to the organic phase and the mixture was filtered. The celite was washed five times with 100 ml of ethyl acetate. The pooled organic fractions were washed twice with 400 ml of a 25% NaCl solution, dried over $MgSO_4$ and evaporated under reduced pressure. The hydrazine N-XVII,3 was used without further purification. The hydrazine N-XVII,3 was dissolved in 116 ml of ethyl formate and 50 ml of dimethylformamide and the mixture was refluxed for 48 hours. The solvent was removed under reduced pressure and the residue was treated with 400 ml of water. The aqueous phase was extracted three times with 200 ml of methylene chloride. The pooled organic fractions were washed twice with 100 ml of water, dried over $MgSO_4$ and evaporated under reduced pressure. The residue was purified by preparative column chromatography (eluent: $CH_2Cl_2$—MeOH: 95/5: Rf: 0.17).

The synthesis of nucleating agent N-XVII 8.5 g (35 mmol) of N-XVII,4 was dissolved in 100 ml of acetone. 24.8 g (0.175 mol) of methyl iodide was added and the reaction mixture was refluxed for 75 minutes. The nucleating agent N-XVII precipitated from the medium. N-XVII was isolated by filtration, washed with acetone and dried (m.p.: 226° C.).

The hydrazides used in accordance with the present invention can be incorporated in the emulsion layer(s) as organic solvent solutions, preferably as methanolic solutions.

The nucleating hydrazine compounds of the present invention are preferably incorporated into the emulsion layer but, alternatively, they can be present in an adjacent hydrophylic layer.

We will now explain in detail the most important other features of the photogarphic material according to the present invention.

Suitable organic resin supports for use in accordance with the present invention include cellulose nitrate film, cellulose acetate film, poly(vinyl acetal) film, polystyrene film, poly(ethylene terephthalate) film, polycarbonate film, polyvinylchloride film or poly-a-olefin films such as polyethylene or polypropylene film. The thickness of such organic resin film is preferably comprised between 0.025 and 0.25 mm.

In a most preferred embodiment the support is a polyethylene terephthalate support, optionally provided with a subbing layer. An example of a suitable subbing layer is a layer containing a polymer containing covalently bound chlorine. Suitable chlorine containing polymers are e.g. polyvinyl chloride, polyvinylidene chloride, a copolymer of vinylidene chloride, an acrylic ester and itaconic acid, a copolymer of vinyl chloride and vinylidene chloride, a copolymer of vinyl chloride, vinylidene chloride and itaconic acid, a copolymer of vinyl chloride, vinyl acetate and vinyl alcohol, A preferred chlorine containing polymer is co(vinylidenechloride-methylacrylate-itaconic acid; 88%/10%/2%). A most suitable subbing layer contains the latter polymer and a colloidal silica such as KIESELSOL 100F (Bayer AG). Optionally to this composition can be added co(methylacrylate-butadiene-itaconic acid) (49/49/2), preferably in a ratio of about 10%. The most favourable adhesion properties are obtained when a subbing layer as described above provided with an additional primer layer containing gelatin (preferably 0.25–0.35 g/m$^2$), Kieselsol 300 F (0.30–0.40 g/m$^2$) and a matting agent on the base of polymethylmethacrylate (average size 2 á 3 mm) at a coverage of about 0.001 g/m$^2$.

The silver halide emulsion or mixture of emulsions of the photographic material in connection with the present invention can be incorporated in one single layer but, alternatively, a double emulsion layer or even a multiple layer pack can be applied.

The halide composition of the silver halide emulsions used in accordance with the present invention is not specifically limited and may be any composition selected from e.g. silver chloride, silver bromide, silver iodide, silver chlorobromide, silver bromoiodide, and silver chlorobromoiodide. In a prefered embodiment however, the photographic material is a graphic arts material, most preferably, a graphic arts recording material, which by definition is suited for the recording of screened images, linework and/or text, and/or printed circuit board patterns, electronically stored in an image-setter or scanner. Graphic arts recording materials preferably use emulsions containing a majority of chloride, preferably between 50 mole % and 95 mole %, most preferably between 65 mole % and 89 mole %, and a low amount of iodide, the remaining halide being bromide.

The photographic emulsion(s) can be prepared from soluble silver salts and soluble halides according to different methods as described e.g. by P. Glafkidés in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). They can be prepared by mixing the halide and silver solutions in partially or fully controlled conditions of temperature, concentrations, sequence of addition, and rates of addition. The silver halide can be precipitated according to the single-jet method, the double-jet method, the conversion method or an alternation of these different methods.

The silver halide particles of the photographic emulsion (s) may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains may comprise a core and a shell, which may have different halide compositions and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in accordance with the present invention.

The average size of the silver halide grains may range from 0.05 to 1.0 micron, preferably from 0.2 to 0.5 micron. The size distribution of the silver halide particles can be homodisperse or heterodisperse.

The silver halide emulsions can be doped with various metal salts or complexes such as Rhodium and Iridium dopants.

The emulsion can be desalted in the usual ways e.g. by dialysis, by flocculation and re-dispersing, or by ultrafiltration.

The light-sensitive silver halide emulsions are preferably chemically sensitized as described e.g. in the above-mentioned "Chimie et Physique Photographique" by P. Glafkidés, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners or by means of reductors e.g. tin compounds as described in GB 789,823, amines, hydrazine derivatives, formamidine-sulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The light-sensitive silver halide emulsions can be spectrally sensitized with proper dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes and complex merocyanine dyes.

The silver halide emulsion(s) for use in accordance with the present invention may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion. Suitable examples are e.g. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are metal salts such as e.g. mercury or cadmium salts and the compounds described in Research Disclosure N° 17643 (1978), Chapter VI.

The fog-inhibiting agents or stabilizers can be added to the silver halide emulsion prior to, during, or after the ripening thereof and mixtures of two or more of these compounds can be used.

Besides the silver halide another essential component of a light-sensitive emulsion layer is the binder. The binder is a hydrophilic colloid, preferably gelatin. Gelatin can, however, be replaced in part or integrally by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic material of the present invention may further comprise various kinds of surface-active agents in the photographic emulsion layer or in another hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Other suitable surfactants include perfluorinated compounds. Such surface-active agents can be used for various purposes e.g. as coating aids, as compounds preventing electric charges, as compounds improving slidability, as compounds facilitating dispersive emulsification, as compounds preventing or reducing adhesion, and as compounds improving the photographic characteristics e.g higher contrast, sensitization, and development acceleration.

Beside the light sensitive emulsion layer(s) the photographic material can contain several non light sensitive layers, e.g. an anti-stress top layer, one or more backing layers, and one or more intermediate layers eventually containing filter- or antihalation dyes that absorb scattering light and thus promote the image sharpness. Suitable light-absorbing dyes are described in i.a. U.S. Pat. No. 4,092,168, U.S. Pat. No. 4,311,787 and DE 2,453,217. One or more backing layers can be provided at the non-light sensitive side of the support. This layers which can serve as anti-curl layer can contain i.a. matting agents e.g. silica particles, lubricants, antistatic agents, light absorbing dyes, opacifying agents, e.g. titanium oxide and the usual ingredients like hardeners and wetting agents.

The backing layer(s) may further contain an antistatic agent. Suitable antistatic polymers for incorporation in a backing layer are disclosed in e.g. *Research Disclosure, April* 1990, Item 31237. Further references on ionic conductive polymers include U.S. Pat. No. 4,585,730, U.S. Pat. No. 4,701,403, U.S. Pat. No. 4,589,570, U.S. Pat. No. 5,045,441, EP-A-391 402 and EP-A-420 226. An antistatic agent can also be incorporated in a separate layer or in a subbing layer. Relatively recently electrically conducting conjugated polymers have been developed that have electronic conductivity. For ecological reasons the coating of antistatic layers should proceed where possible from aqueous solutions by using as few as possible organic solvents. The production of antistatic coatings from aqueous coating compositions being dispersions of polythiophenes in the presence of polyanions is described in EP 0 440 957.

The photographic elements in connection with the present invention may further comprise various other additives such as e.g. compounds improving the dimensional stability of the photographic element, UV-absorbers, spacing agents and plasticizers.

Suitable additives for improving the dimensional stability of the photographic elements are e.g. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth) acrylates, sulphoalkyl (meth)acrylates, and styrene sulphonic acids.

Spacing agents can be present, preferably in the top protective layer. In general the average particle size of such spacing agents is comprised between 0.2 and 10 micron. They can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made e.g. of polymethyl methacrylate, of copolymers of acrylic acid and methyl methacrylate, and of hydroxypropylmethyl cellulose hexahydrophthalate. Other suitable spacing agents have been described in U.S. Pat. No. 4,614,708.

The photographic materials according to the present invention can, after proper exposure, be processed by any means or any chemicals known in the art depending on their particular application. Preferably however, they are processed in so-called "Rapid Access" chemicals, comprising a conventional Phenidone/hydroquinone developing solution or an ascorbic acid developing solution, and a conventional sodium- or ammonium thiosulphate containing fixing solution. As explained above their is no need for special "hard dot Rapid Access" developers, altough in principle the materials of the present invention can be developed therein. The development time is usually between 10 and 30 seconds at a temperature of about 35° C.

The present invention will now be illustrated by the following examples without however being limited thereto.

EXAMPLES

Example 1 preparation of the photographic samples

To an aqueous gelatin solution containing sodium chloride, an aqueous solution of silver nitrate and an aqueous halide solution containing potassium bromide, sodium chloride, $6.0 \times 10^{-7}$ mol/mol silver of $Na_3RhCl_6$ and $7.0 \times 10^{-7}$ mol/mol silver of $K_4IrCl_6$ were added whilst stirring according to the double jet precipitation method to form silver chlorobromide emulsion grains having an average grain size of 0.24 μm (variation coefficient: 19%) and a chloride content of 70 mol %.

Thereafter, the emulsion was washed after a conventional flocculation step, and then redispersed with 27 g gelatin per mol of silver halide. The resulting emulsion was adjusted to pH 5.5 and then chemically sensitized at 50° C. by adding 6 mg/mol of silver halide of chloroauric acid and 10 mg/mol of silver halide of sodium thiosulfate and then digesting during three hours. The emulsion was stabilized with $9.0 \times 10^{-3}$ mol/mol silver of 4-hydroxy-6-methyl-1,3,3a,7-tetraazaindene, and finally spectrally sensitized to the blue spectral region with dye D-1.

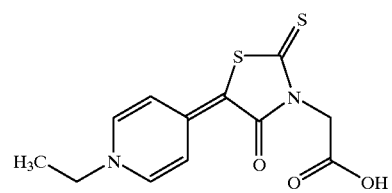

D-1

Then the emulsion was divided in aliquot samples and to the invention samples nucleating agents according to following tables 3 and 4 were added as methanol solutions in concentrations optimized for each agent in preliminary experiments. A control sample contained no nucleating agent.

The different emulsion samples were each coated onto a polyethylene terephthalate film support at 4 g/m² of silver, and were overcoated with a gelatinous protective layer containing formaldehyde as hardening agent, 50 mg/m² of 1-p-carboxy-phenyl-3-pyrazolidone, 2.5 mg/m² of a fluorine-containing surfactant and 10 mg/m² of poly (methylmethacrylate) matting agent. Finally, the film samples were dried.

photographic evaluation

Each photographic sample was exposed to a xenon flash lamp (light emitting time: $10^{-5}$ s) through both a step wedge and a filter having its peak of transmittance at 488 nm, and then developed for 30 seconds at 35° C. by means of a Developer A (see table 1). Another exposed sample was developed for 35 seconds at 35° C. by means of a Developer B (table 2). After development the samples were fixed in a conventional fixer containing ammonium thiosulphate, washed and dried. The processing took place in a Rapiline 66T3 processor, marketed by Agfa-Gevaert N. V.

TABLE 1

| Developer A | |
|---|---|
| Potassium carbonate | 17.0 g |
| Potassium hydroxide | 5.3 g |
| Potassium sulfite | 49.2 g |
| Hydroquinone | 20.0 g |
| 1-phenyl-3-pyrazolidone | 0.48 g |
| Potassium bromide | 10.0 g |
| 1-phenyl-5-mercaptotetrazole | 0.03 g |
| Water to make | 1 l |

The pH of Developer A was adjusted to 10.5 with potassium hydroxide.

TABLE 2

| Developer B | |
|---|---|
| Na-L-ascorbate | 39 g |
| Potassium hydroxide | 9.1 g |
| Potassium bromide | 5.0 g |
| Potassium carbonate | 26.0 g |
| Sodium metabisulfite | 20.0 g |
| Boric acid | 38.0 g |
| N-methyl-p-aminophenole | 7.5 g |
| Water to make | 1 l |

The pH of Developer B was adjusted to 10.1 with potassium hydroxide.

The sensitometric data of the samples developed in developer A are represented in table 3; the sensitometric data of the samples developed in developer B are represented in table 4. The gamma (γ), being a measure for the contrast of an image and an important parameter for image quality in graphic films, was determined between two points on the sensitometric curve, namely those corresponding to (fog+density 0.1) and (fog+density 0.5).

TABLE 3

| Nucleator | Concentration (mmole/mole Ag) | fog | γ | Note |
|---|---|---|---|---|
| None | — | 0.03 | 3.1 | Comparison |
| Compound N-I | 4.6 | 0.03 | 5.3 | Invention |
| Compound N-VI | 2.0 | 0.03 | 8.0 | Invention |
| Compound N-VII | 4.0 | 0.04 | 12.3 | Invention |
| Compound N-X | 8.0 | 0.04 | 4.7 | Invention |
| Compound N-XVII | 5.8 | 0.04 | 4.7 | Invention |

TABLE 4

| Nucleator | Concentration (mmole/mole Ag) | fog | γ | Note |
|---|---|---|---|---|
| None | — | 0.04 | 3.0 | Comparison |
| Compound N-I | 4.6 | 0.04 | 14.4 | Invention |
| Compound N-VI | 2.0 | 0.04 | 9.3 | Invention |
| Compound N-VII | 4.0 | 0.04 | 15.1 | Invention |
| Compound N-X | 8.0 | 0.04 | 7.7 | Invention |
| Compound N-XVII | 7.8 | 0.05 | 6.5 | Invention |

From the results summarized in the tables it is clear that the compounds of the invention clearly show an important increase in contrast leading to enhanced image quality for graphic applications.

Example 2 preparation of photographic samples

Emulsion and coated samples were prepared in a manner similar to example 1. The nucleators added to the individual emulsion layers and their respective amounts used are represented in table 5.

photographic evaluation

Each sample was exposed on a Ar-laser Crosfield scanner leading to a 50% dot pattern after developing in Developer A, fixing, washing and drying in a Rapiline 66T3 (Agfa) processor. The dot quality was evaluated with a magnifying glass in order to examine them for definition and smoothness. The reproduced dot quality was judged by an arbitrary scale ranging from 1 to 5. Grade 1 represented a poor, fuzzy, continuous tone type dot. Grade 5 represented an excellent, hard "lith" type dot. The results are summarized in table 5.

TABLE 5

| Nucleator | Concentration (mmole/mole Ag) | Dot Quality | Note |
|---|---|---|---|
| None | — | 1 | Comparison |
| Compound N-VI | 2.0 | 4 | Invention |
| Compound N-VII | 4.0 | 5 | Invention |
| Compound N-X | 8.0 | 3 | Invention |

The samples containing the compounds of the present invention clearly showed significantly improved dot characteristics as compared to the film sample without a nucleator.

Example 3 preparation of photographic samples

The emulsion was prepared in a way similar to example 1 and 2 with the exception that the emulsion was red sensitized with dye D-2 instead of D-1. The nucleating agents N-VI and N-VII were added (see table 4).

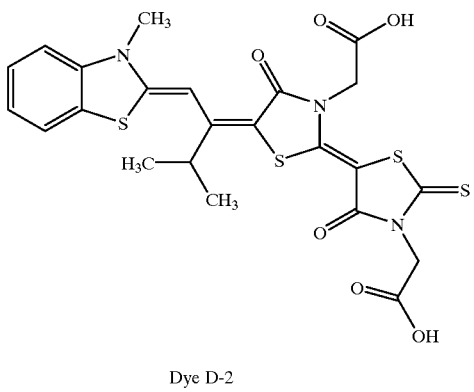

Dye D-2

The samples were coated in a way identical to example 1. They were exposed through a step wedge to a xenon flash provided with a 622 nm filter. They were processed according to example 1.

photographic evaluation

The sensitometric data of the samples developed in developer A are represented in table 6. The sensitometric data of the samples developed in developer B are represented in table 7.

TABLE 6

| nucleator | conc. (mmol/mol Ag) | fog | γ | note |
|---|---|---|---|---|
| none | — | 0.03 | 3.1 | comp. |
| comp. N-VI | 2.0 | 0.04 | 7.4 | invent. |
| comp. N-VII | 4.0 | 0.04 | 10.7 | invent. |

TABLE 7

| nucleator | conc. (mmol/mol Ag) | fog | γ | note |
|---|---|---|---|---|
| none | — | 0.04 | 3.0 | comp. |
| comp. N-VI | 1.0 | 0.04 | 7.9 | invent. |
| comp. N-VII | 4.0 | 0.04 | 11.3 | invent. |

The compounds of this invention clearly demonstrate an important increase in contrast leading to enhanced image quality for graphic applications.

The samples were exposed on an imagesetter ACCUSET 100 (Agfa) equipped with a red laserdiode leading to a 50% dot pattern after developing in developer A, fixing washing and drying in a Rapiline 66T3 processor (Agfa). The dot quality was evaluated with a magnifying glass in order to examine them for definition and smoothness. Grade 1 represents a poor, fuzzy, continuous tone type dot. Grade 5 represents an excellent, hard "lith" type dot. Besides an excellent image quality a high gradation leads also to a high Dmax at exact rendering. The results are summarized in table 8.

TABLE 8

| nucleator | conc. (mmol/mol Ag) | dot quality | Dmax | note |
|---|---|---|---|---|
| none | — | 1 | 3.1 | comp. |
| comp. N-VI | 2.0 | 4 | 4.2 | invent. |
| comp. N-VII | 4.0 | 5 | 4.7 | invent. |

The samples provided with the compounds of this invention exhibited improved dot characteristics and a high Dmax at exact rendering as compared to the sample without nucleator.

Example 4 preparation of emulsion samples

To an aqueous gelatin solution containing sodium chloride, an aqueous solution of silver nitrate and an aqueous halide solution containing potassium bromide, sodium chloride, $1.9 \times 10^{-7}$ mol/mol silver of $Na_3RhCl_6$ and $9.8 \times 10^{-7}$ mol/mol silver of $K_4IrCl_6$ were added whilst stirring according to the double jet precipitation method to form silver chlorobromide emulsion grains having an average grain size of 0.27 μm (variation coefficient: 19%) and a chloride content of 64 mol %.

Thereafter, the emulsion was washed after a conventional flocculation step, and then redispersed with 27 g gelatin per mol of silver halide. The resulting emulsion was adjusted to pH 5.5 and then chemically sensitized at 50° C. by adding 6 mg/mol of silver halide of chloroauric acid and 10 mg/mol of silver halide of sodium thiosulfate and then digesting during three hours. The emulsion was stabilized with $9.0 \times 10^{-3}$ mol/mol silver of 4-hydroxy-6-methyl-1,3,3a,7-tetraazaindene, $5.9 \times 10^{-5}$ mol/mol silver of 1-(4-carboxyphenyl)-5-mercaptotetrazole, and $6.7 \times 10^{-5}$ mol/mol silver of 1-phenyl-5-mercaptotetrazole. Then the emulsion was infra-red sensitized by adding dye D-3 in an amount of $5.0 \times 10^{-4}$ mol/mol silver and supersensitizer S-1 in an amount of $5.4 \times 10^{-3}$ mol/mol silver. The nucleating agent N-VII was added as methanolic solution.

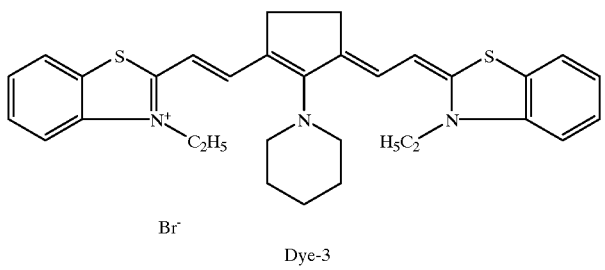

Dye-3

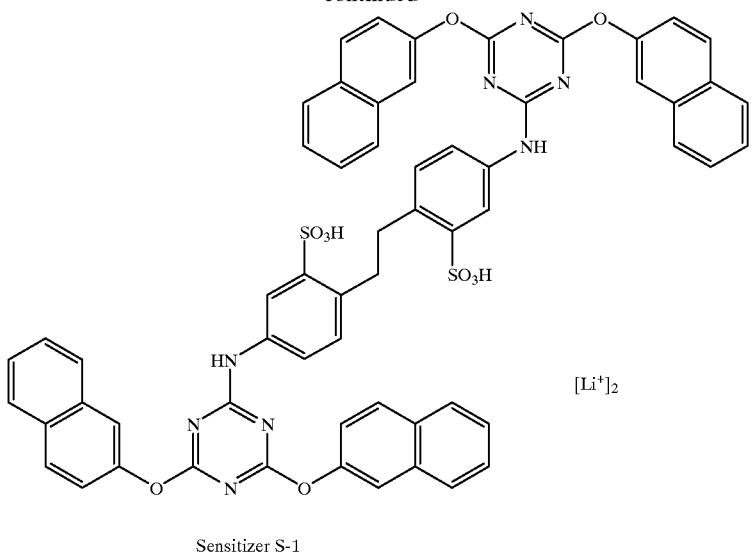

Sensitizer S-1

The samples were coated in a way similar to example 1. Then they were exposed to an infra-red laserdiode imagesetter CG9400 (Agfa) and then developed for 30 seconds at 35° C. with developer A. Thereafter they were subjected to fixation, washing and drying in a Rapiline 66T3 processor (Agfa).

photographic evaluation

The dot quality was evaluated with a magnifying glass in order to examine them for definition and smoothness. Grade 1 represents a poor, fuzzy, continuous tone type dot. Grade 5 represents an excellent, hard "lith" type dot. Besides an excellent image quality a high gradation leads also to a high Dmax at exact rendering. The results are summarized in table 9.

TABLE 9

| nucleator | conc. (mmol/mol Ag) | dot quality | Dmax | note |
|---|---|---|---|---|
| none | — | 1 | 2.7 | comp. |
| comp. N-VII | 4.0 | 5 | 3.8 | invent. |

The sample with the nucleator exhibited significant improved dot characteristics and a high Dmax at exact rendering as compared to the sample without nucleator.

Example 5 preparation of the emulsion

To an aqueous gelatin solution containing sodium chloride, an aqueous solution of silver nitrate and an aqueous halide solution containing ammonium bromide, sodium chloride, $2.3 \times 10^{-7}$ mol/mol silver of $Na_3RhCl_6$ and $3.0 \times 10^{-7}$ mol/mol silver of $Na_2IrCl_6$ were added with stirring in accordance with a double jet method to form silver chlorobromide grains having an average grain size of 0.27 μm (variation coefficient: 19%) and a chloride content of 64 mol %.

Thereafter, the emulsion was washed using a conventional flocculation method, and then redispersed with 27 g/mol silver of gelatin. The resulting emulsion was adjusted to pH 5.0 and then chemically sensitized at 50° C. by adding 3.9 mg/mol silver of chloroauric acid and 3.3 mg/mol silver of sodium thiosulfate and digesting during three hours. The emulsion was stabilized with $8.4 \times 10^{-3}$ mol/mol silver of 4-hydroxy-6-methyl-1,3,3a,7-tetraazaindene, spectrally sensitized with dye D-2 in an amount of $4.0 \times 10^{-4}$ mol/mol silver. The nucleating agents were added as methanol solutions either in the emulsion layer or the top layer.

The emulsions were coated onto a polyethylene terephthalate film support at 4 g per square meter of silver and were overcoated with an aqueous gelatin anti-abrasion layer containing formaldehyde as hardening agent, 25 mg per square meter of 1-p-carboxy-phenyl-3-pyrazolidone, 2.5 mg per square meter of a fluorine-containing surfactant and 10 mg per square meter of poly(methyl methacrylate) matting agent. After the coating the film samples were dried.

Exposure and Photographic Processing

Each sample was exposed to a xenon flash lamp (light emitting time: $10^{-5}$ s) through both a step wedge and a filter having its peak at 622 nm, and then developed for 30 seconds at 35° C. with the hydroquinone/Phenidone developer G101c (Agfa). Thereafter, it was subjected successively to fixation in a conventional fixation bath, washing and drying operations. The processing took place in a Rapiline 66T3 processor (Agfa).

photographic evaluation

An indication showing the contrast of an image (a gamma value γ) was defined as the slope of a straight line connecting two points on the sensitometric curve, namely those corresponding to (fog+density 0.1) and (fog+density 0.5). The photographic material has more contrasty photographic characteristics the greater the gamma value. The sensitometric data of the samples are represented in table 10.

TABLE 10

| Nucleator | Concentration (mmole/mole Ag) | Layer | Fog | γ | Note |
|---|---|---|---|---|---|
| None | — | — | 0.04 | 3.6 | Comparison |
| Comp. N-XIX | 2 | EM | 0.04 | 7.7 | Invention |
| " | 2 | top | 0.04 | 6.9 | Invention |
| " | 4 | top | 0.04 | 10.5 | Invention |
| Comp. N-XX | 2 | EM | 0.04 | 4.1 | Invention |
| " | 2 | top | 0.04 | 4.4 | Invention |
| " | 4 | top | 0 04 | 7.52 | Invention |
| Comp. N-XXI | 2 | EM | 0.04 | 7.9 | Invention |
| " | 2 | top | 0.04 | 5.5 | Invention |

TABLE 10-continued

| Nucleator | Concentration (mmole/mole Ag) | Layer | Fog | γ | Note |
|---|---|---|---|---|---|
| " | 4 | top | 0.04 | 10.7 | Invention |
| Comp. N-XXII | 2 | EM | 0.04 | 9.5 | Invention |
| " | 4 | EM | 0.05 | 9.2 | Invention |
| " | 2 | top | 0.04 | 11.2 | Invention |
| " | 4 | top | 0.03 | 10.5 | Invention |
| " | 8 | top | 0.05 | 13.0 | Invention |
| Comp. N-XXIII | 2 | EM | 0.04 | 8.3 | Invention |
| " | 3 | EM | 0.04 | 9.3 | Invention |
| " | 4 | EM | 0.04 | 8.0 | Invention |
| " | 2 | top | 0.04 | 8.4 | Invention |
| " | 3 | top | 0.04 | 8.0 | Invention |
| " | 4 | top | 0.04 | 7.0 | Invention |
| Comp. N-XXIV | 3.3 | top | 0.04 | 9.6 | Invention |
| " | 5.1 | top | 0.04 | 9.9 | Invention |
| " | 6.6 | top | 0.04 | 9.5 | Invention |

The samples containing the compounds of this invention clearly show an important increase in contrast leading to enhanced image quality for graphic applications.

The samples were exposed on a red laserdiode imagesetter Accuset 1000 (Agfa) leading to a 50%-dot pattern after developing in G101c (Agfa), fixing, washing and drying in a Rapiline 66T3 (Agfa) processor. The dot quality was evaluated as in examples 2 and 3. The results are summarized in table 11.

TABLE 11

| Nucleator | Concentration (mmole/mole Ag) | Layer | Dot quality | Note |
|---|---|---|---|---|
| None | — | | 1 | Comparison |
| Comp. N-XIX | 2 | EM | 5 | Invention |
| " | 2 | top | 3 | Invention |
| " | 4 | top | 5 | Invention |
| Comp. N-XX | 2 | EM | 3 | Invention |
| " | 2 | top | 4 | Invention |
| " | 4 | top | 5 | Invention |
| Comp. N-XXI | 2 | EM | 5 | Invention |
| " | 2 | top | 3 | Invention |
| " | 4 | top | 5 | Invention |
| Comp. N-XXII | 2 | EM | 5 | Invention |
| " | 2 | top | 5 | Invention |
| " | 4 | top | 5 | Invention |
| " | 8 | top | 5 | Invention |
| Comp. N-XXIII | 2 | EM | 4 | Invention |
| " | 3 | EM | 4 | Invention |
| " | 4 | EM | 4 | Invention |
| " | 2 | top | 4 | Invention |
| " | 3 | top | 5 | Invention |
| " | 4 | top | 5 | Invention |
| " | 3.3 | top | 4 | Invention |
| " | 5.1 | top | 5 | Invention |
| " | 6.6 | top | 5 | Invention |

The samples containing the compounds of this invention clearly show significant improved dot characteristics as compared to the film sample without the nucleator.

Example 6 preparation of photographic samples

Emulsion and coated samples were prepared in a manner similar to example 5.

photographic evaluation

Each sample was exposed on a red laserdiode imagesetter Accuset 1000 (Agfa) leading to a 50%-dot pattern after developing in G101c (Agfa), fixing, washing and drying in a Rapiline 66T3 (Agfa) processor. The dot quality was evaluated with a magnifying glass in order to examine the samples for definition and smoothness and the solid density was measured (practical density). The results are summarized in table 12.

TABLE 12

| Nucleator | Concentration (mmole/mole Ag) | Layer | Dot quality | Practical density | Note |
|---|---|---|---|---|---|
| None | — | | 1 | 3.4 | Comparison |
| Comp. N-XIX | 4 | EM | 5 | 4.7 | Invention |
| " | 3 | top | 5 | 3.8 | Invention |
| " | 6 | top | 5 | 4.3 | Invention |
| Comp. N-XXIII | 3 | top | 5 | 4.7 | Invention |

The use of the compounds of this invention leads to strongly improved dot sharpness and higher practical density as compared to the film samples without the nucleator.

Example 7 preparation of the photographic samples

To an aqueous gelatin solution containing sodium chloride, an aqueous solution of silver nitrate and an aqueous halide solution containing ammonium bromide, sodium chloride, $2.3 \times 10^{-7}$ mol/mol silver of $Na_3RhCl_6$ and $3.0 \times 10^{-7}$ mol/mol silver of $Na_2IrCl_6$ were added with stirring in accordance with a double jet method to form silver chlorobromide grains having an average grain size of 0.27 μm (variation coefficient: 19%) and a chloride content of 64 mol %.

Thereafter, the emulsion was washed using a conventional flocculation method, and then redispersed with 27 g/mol silver of gelatin. The resulting emulsion was adjusted to pH 5.5 and then chemically sensitized at 50° C. by adding 3.9 mg/mol silver of chloroauric acid and 3.3 mg/mol silver of sodium thiosulfate and digesting during three hours. The emulsion was stabilized with $8.4 \times 10^{-3}$ mol/mol silver of 4-hydroxy-6-Methyl-1,3,3a,7-tetraazaindene, spectrally sensitized with dye D-1 in an amount of $1.2 \times 10^{-3}$ mol/mol silver. The nucleating agents were added as methanolic solutions either in the emulsion layer or the top layer.

The emulsions were coated onto a polyethylene terephthalate film support at 4 g per square meter of silver and were overcoated with an aqueous gelatin anti-abrasion layer containing formaldehyde as hardening agent, 25 mg per square meter of 1-p-carboxy-phenyl-3-pyrazolidone, 2.5 mg per square meter of a fluorine-containing surfactant and 10 mg per square meter of poly(methyl methacrylate) matting agent. After the coating the film samples were dried.

exposure and photographic processing

Each sample was exposed to a xenon flash lamp (light emitting time: $10^{-5}$ s.) through both a step wedge and a filter having its transmission peak at 488 nm, and then developed for 30 seconds at 35° C. with developer G101c (Agfa). Thereafter, it was subjected successively to fixation in a conventional fixation bath, washing and drying operations. The processing took place in a Rapiline 66T3 processor (Agfa).

photographic evaluation

The sensitometric data of the samples are represented n table 13.

TABLE 13

| Nucleator | Concentration (mmole/mole Ag) | Layer | Fog | γ | Note |
|---|---|---|---|---|---|
| None | — | | 0.04 | 3.5 | Comparison |
| Comp. N-XIX | 2.9 | top | 0.04 | 9.2 | Invention |
| " | 4.4 | top | 0.04 | 13.0 | Invention |
| Comp. N-XX | 3.3 | top | 0.04 | 12.5 | Invention |
| " | 5.1 | top | 0.04 | 13.2 | Invention |

The samples containing the compounds of this invention clearly demonstrate an important increase in contrast leading to enhanced image quality for graphic applications.

Each sample was exposed on a Ar-laser Crosfield scanner leading to a 50% dot pattern after developing in Developer A, fixing, washing and drying in a Rapiline 66T3 (Agfa) processor. The dot quality was evaluated as in previous examples. The results are summarized in table 14.

TABLE 14

| Nucleator | Concentration (mmole/mole Ag) | Layer | Dot quality | Note |
|---|---|---|---|---|
| None | — | | 1 | Comparison |
| Comp. N-XXII | 2.9 | top | 4 | Invention |
| " | 4.4 | top | 5 | Invention |
| Comp. N-XXIII | 3.3 | top | 5 | Invention |
| " | 5.1 | top | 5 | Invention |

The samples containing the compounds of this invention clearly show significant improved dot characteristics as compared to the film sample without the nucleator.

Example 8 preparation of photographic samples

To an aqueous gelatin solution containing sodium chloride, an aqueous solution of silver nitrate and an aqueous halide solution containing potassium bromide, sodium chloride, $2.1 \times 10^{-7}$ mol/mol silver of $Na_3RhCl_6$ and $4.3 \times 10^{-7}$ mol/mol silver of $Na_2IrCl_6$ were added with stirring in accordance with a double jet method to form silver chlorobromide grains having an average grain size of 0.27 μm (variation coefficient: 19%) and a chloride content of 64 mol %.

Thereafter, the emulsion was washed using a conventional flocculation method, and then redispersed with 27 g/mol silver of gelatin. The resulting emulsion was adjusted to pH 5.0 and then chemically sensitized at 50° C. by adding $15 \times 10^{-6}$ mol/mol silver of chloroauric acid, $161 \times 10^{-6}$ mol/mol silver of KSCN and 3.4 mg/mol silver of sodium thiosulfate and digesting during three hours. The emulsion was stabilized with $7.1 \times 10^{-3}$ mol/mol silver of 4-hydroxy-6-methyl-1,3,3a,7-tetraazaindene, spectrally sensitized with infra-red sensitizing dye D-3 in an amount of $4.7 \times 10^{-5}$ mol/mol silver and with the supersensitizer S-1 in an amount of $1.3 \times 10^{-3}$ mol/mol silver. The nucleating agents were added as methanolic solutions in the top layer.

The emulsions were coated onto a polyethylene terephthalate film support at 4 g per square meter of silver and were overcoated with an aqueous gelatin anti-abrasion layer containing formaldehyde as hardening agent, 25 mg per square meter of 1-p-carboxy-phenyl-3-pyrazolidone, 2.5 mg per square meter of a fluorine-containing surfactant and 10 mg per square meter of poly(methyl methacrylate) matting agent. After the coating the film samples were dried.

exposure and photographic processing

Each sample was exposed to an infrared laserdiode emitting at 780 nm through a step wedge, and then developed for 30 seconds at 35° C. with developer G101c (Agfa). Thereafter, it was subjected successively to fixation in a conventional fixation bath, washing and drying operations. The processing took place in a Rapiline 66T3 processor (Agfa).

photogaphic evaluation

The sensitometric data of the samples are represented in table 15.

TABLE 15

| Nucleator | Concentration (mmole/mole Ag) | Layer | Fog | γ | Note |
|---|---|---|---|---|---|
| None | — | | 0.04 | 1.9 | Comparison |
| Comp. N-XXII | 2.9 | top | 0.04 | 4.7 | Invention |
| " | 4.4 | top | 0.04 | 6.4 | Invention |
| Comp. N-XXIII | 3.3 | top | 0.04 | 6.0 | Invention |
| " | 5.1 | top | 0.04 | 6.7 | Invention |

The samples containing the compounds of this invention clearly show an important increase in contrast leading to enhanced image quality for graphic applications.

We claim:

1. Photographic material comprising a support, at least one emulsion layer, and optionally one or more other hydrophylic layers, characterized in that said emulsion layer or another hydrophilic layer adjacent to said emulsion layer contains a compound according to general formula I:

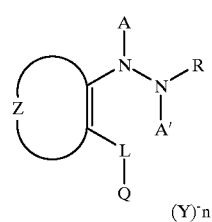

(Formula I)

wherein

1) R represents a member selected from the group consisting of $COR^1$, $SO_2R^2$, $SOR^3$, $POR^4R^5$ and $COCOR^6$; each of $R^1$ and $R^6$ independently represents hydrogen, an alkyl group, an aryl- or heteroarylgroup, $OR^7$, or $NR^8R^9$; each of $R^2$ and $R^3$ independently represents an alkylgroup, an aryl- or heteroarylgroup, $OR^7$ or $NR^8R^9$; each of $R^4$ and $R^5$ indepedently represents one of the significances given for $R^2$ or they may constitute together the necessary atoms to close a ring; $R^7$ represents an alkylgroup, an aryl- or heteroarylgroup; each of $R^8$ and $R^9$ independently represents hydrogen, an alkyl group or an aryl- or heteroaryl-group or they may constitute together the necessary atoms to form a ring;

2) each of A and A" independently represent a hydrogen, a group capable of yielding hydrogen under alkaline photographic processing conditions or a $SO_2R^{10}$ group, provided that, if A is $SO_2R^{10}$, A' is a hydrogen and vice versa; $R^{10}$ has one of the significances given for $R^2$;

3) L is a divalent linking group consisting of a linear chain having at most two atoms in said chain;

4) Q is a cationic nitrogen containing aromatic heterocyclic ring;

5) $Y^-$ is a negatively charged counterion to compensate the positive charge of Q;

n is 0 if the compound according to formula I is an inner salt or an integer equal to the positive charge of Q, and 6) Z represents the necessary atoms to form an aromatic or heteroaromatic ring.

2. Photographic material according to claim 1 wherein Q is a member selected from the group consisting of a pyridinium, a quinoliniumm and an isoquinolinium.

3. Photographic material according to claim 2 wherein Q is a pyridinium substituted on the $N^+$ with a $C_5$ to $C_8$ alkyl group.

4. Photographic material according to claim 1 wherein said divalent linking group L is chosen from the group consisting of a monoatomic group, an ethylene group, a O-methylene group and a S-methylene group.

5. Photographic element according to any of the previous claims wherein said photographic material is a graphic arts recording material.

6. A compound according to general formula I

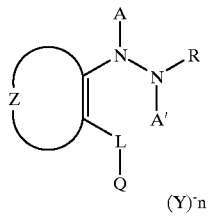

(Formula I)

wherein

1) R represents a member selected from the group consisting of $COR^1$, $SO_2R^2$, $SOR^3$, $POR^4R^5$ and $COCOR^6$; each of $R^1$ and $R^6$ independently represents hydrogen, an alkyl group, an aryl- or heteroarylgroup, $OR^7$, or $NR^8R^9$; each of $R^2$ and $R^3$ independently represents an alkylgroup, an aryl- or heteroarylgroup, $OR^7$ or $NR^8R^9$; each of $R^4$ and $R^5$ indepedently represents one of the significances given for $R^2$ or they may constitute together the necessary atoms to close a ring; $R^7$ represents an alkylgroup, an aryl- or heteroarylgroup; each of $R^8$ and $R^9$ independently represents hydrogen, an alkyl group or an aryl- or heteroaryl-group or they may constitute together the necessary atoms to form a ring;

2) each of A and A" independently represent a hydrogen, a group capable of yielding hydrogen under alkaline photographic processing conditions or a $SO_2R^{10}$-group, provided that, if A is a $SO_2R^{10}$, A' is a hydrogen and vice versa; $R^{10}$ has one of the significances given for $R^2$;

3) L is a divalent linking group consisting of a linear chain having at most two atoms in said chain;

4) Q is a cationic nitrogen containing aromatic heterocyclic ring;

5) $Y^-$ is a negatively charged counterion to compensate the positive charge of Q;

n is 0 if the compound according to formula I is an inner salt or an integer equal to the positive charge of Q, and 6) Z represents the necessary atoms to form an aromatic or heteroaromatic ring.

7. A compound according to claim 6 wherein Q is a member selected from the group consisting of a pyridinium, a quinolinium and an isoquinolinium.

8. A compound according to claim 7 wherein Q is a pyridinium substituted on the $N^+$ with a $C_5$ to $C_8$ alkyl group.

9. Photographic material according to claim 6 wherein said divalent linking group L is chosen from the group consisting of a monoatomic group, an ethylene group, a O-methylene group and a S-methylene group.

* * * * *